United States Patent [19]

Chung

[11] Patent Number: 5,367,094
[45] Date of Patent: Nov. 22, 1994

[54] CONVENIENT PROCESS FOR THE PREPARATION OF CHIRAL OR RACEMIC PHENYLALANINOLS AND THEIR N-BLOCKED DERIVATIVES

[75] Inventor: Dae-won Chung, Parsippany, N.J.
[73] Assignee: Yukong, Ltd., Seoul, Rep. of Korea
[21] Appl. No.: 72,161
[22] Filed: Jun. 4, 1993
[51] Int. Cl.$^5$ .................. C07C 209/68; C07C 271/16
[52] U.S. Cl. ...................................... 560/29; 564/142; 564/355
[58] Field of Search .................. 564/355, 142; 560/29

[56] References Cited

U.S. PATENT DOCUMENTS 3,084,099  4/1963  Hayes et al. .................. 564/357 X
4,994,617  2/1991  Aubard et al. .................. 564/355

Primary Examiner—Richard L. Raymond
Attorney, Agent, or Firm—Omri M. Behr; Matthew J. McDonald

[57] ABSTRACT

This invention pertains to an improved process for preparing chiral or racemic phenylalaninol (PAO) by hydrogenation of L(+)- or racemic 2-amino-1-phenyl-1,3-propanediol (APPD) in the presence of a strong volatile acid. Furthermore, a more valuable form of PAO such like N-blocked PAO was found to be directly produceable from the hydrogenation mixture without isolation of PAO, when a volatile acid was used as the medium of the hydrogenation reaction.

12 Claims, No Drawings

CONVENIENT PROCESS FOR THE PREPARATION OF CHIRAL OR RACEMIC PHENYLALANINOLS AND THEIR N-BLOCKED DERIVATIVES

BACKGROUND OF THE INVENTION

The present invention relates to a convenient method for preparing optically active or racemic phenylalaninols and their derivatives. More specifically the invention pertains to a method for producing those compounds by hydrogenation of 2-amino-1-phenyl-1,3-propanediol (APPD) in the presence of a strong volatile acid.

Optically pure phenylalaninols are interesting compounds useful as optical-resolution agents (Japanese Patent 5959651 ), renin inhibitors (Biochem. Biophys. Res. Commun. 143,44 (1987)), and C-terminal protecting group in peptide synthesis (J. Chem. Soc. Perkin Trans. I, 535 (1988)).

The classical method of preparing phenylalaninol is the reduction of a phenylalanine derivative by lithium aluminium or borane hydrides. However, this is a rather expensive process and dependent on the availability of L- or D-phenylalanine. Another approach to prepare D-phenylalaninol is starting from L(+)-2-amino-1-phenyl-1,3-propanediol(APPD), which can be obtained as the by-product from chloramphenicol or thiamphenicol synthesis.

There are many possible methods for hydrogenating the hydroxyl group at benzyl position of APPD. For example, U.S. Pat. No. 3,084,099 issued to Hays et al. describes a method of preparing 1-benzyl-iso-propyl amine from 1phenyl-2-methyl-2-amino-propanol by hydrogenation in 57% hydriodic acid with red phosphorous. However, the strongly acidic condition of this system may induce iodination of other hydroxyl groups. In fact, the hydrogenation of APPD in the above conditions produced 1-phenyl-2-amino-3-iodopropane instead of phenylalaninol, as disclosed in Japanese Patent 3910914. Other approaches were made by two independent groups, Boerner et al. prepared D-phenylalaninol from L(+)-APPD by 4 steps with a total yield of 31% (Pharmazie 45, 531 (1990)). On the other hand, the hydrogenation of L(+)-APPD in the presence of sulfuric acid was found to give D-phenylalaninol (D-PAO)in 73–85% yield (Hashizume, Japanese Patent 63255254). It is obvious that the latter is quite cost-effective. However, in this process, it is necessary to use excess amounts of base to neutralize the reaction mixture for the recovery of D-PAO because an excess amount of sulfuric acid is used. When the pH of the reaction mixture is adjusted to above 11, large amounts of salts are produced and some of them, including small amount of D-PAO, are precipitated. This phenomenon makes the work-up process very complicated. Furthermore, it makes it impossible to derivatize phenylalaninol into desired forms such as N-terminal blocked phenylalaninols without isolation of phenylalaninol.

In order to overcome these disadvantages, it would be desirable to provide an improved process for preparing optically active phenylalaninol or their derivatives, and for preparing N-blocked phenylalaninols without isolation of phenylalaninol or their derivatives.

SUMMARY OF THE INVENTION

The present invention is directed to the hydrogenation of chiral or racemic 2-amino-1-phenyl-1,3-propanediols (APPD) in a strong volatile acid, suitably trifluoroacetic acid (TFA) to produce corresponding phenylalaninols. The present invention affords higher reactivity than the prior art (JP 63255254), with no side reactions or need to remove by-products. In another embodiment, the invention is directed to the direct derivatization of D-PAO without its prior isolation.

L( +)-2-amino-1-phenyl-1,3-propanediol or its ring substituted derivatives can be converted into the corresponding phenylalaninols by hydrogenation in the presence of acid.

APPD or its derivatives have the formula (1):

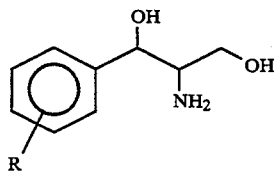

wherein R is H, alkyl of $C_1$-$C_7$, or halogen, suitably bromine, chlorine, fluorine, and iodine.

Among many organic or inorganic acids investigated, TFA gave the best result in a viewpoint of reactivity, lack of side reactions, and ease of work-up process. The reactions were carried out both under high pressure and merely by bubbling in hydrogen gas.

DETAILED DESCRIPTION OF THE INVENTION

Various experiments were carried out in which APPD of general formula (1) was dissolved in a variety of strong acids, volatile and otherwise, such as sulfuric acid, hydrochloric acid, hydriodic acid, p-toluenesulfuric acid, phosphoric acid, acetic acid, trichloroacetic acid (TCA) or TFA.

The reactions were carried out with or without the addition of a suitable solvent, for example water or ethanol. The catalyst (Pd/C or Pt/C) was then added. The catalyst is then added, and the reaction carried out under high pressure of up to 5 atmospheres or merely by bubbling in the hydrogen gas at a certain temperature, suitably between about 25° and 100° C. After a certain time, say about 12 to about 36, suitably about 24 hours, the conversion was determined by HPLC. Then, volatile acid, where present, such as acetic acid, TCA or TFA was removed by evaporation and recovered by condensation. The reaction mixture was diluted with water and catalyst is filtered off. The pH of the filtrate was adjusted to over 13. The isolation of PAO of general formula (2), was carried out by recrystallization or distillation.

Direct derivatization was carried out in the reaction mixture. This was cooled at 4° C., and a suitable derivatizing agent, for example benzyl chloroformate was added dropwise, whereby the N-blocked phenylalaninol was precipitated. After filtration, white crystals were obtained by recrystallization in water/methanol (1:1).

The following examples are illustrative embodiments of this invention. However, these examples are for illustrative purposes only and should not be construed as limitations upon the invention.

EXAMPLE 1

1 ml of concentrated sulfuric acid was slowly added to 15 ml of water, and 75 mg of 5% Pd/C and 1 g of L(+)-2-amino-1-phenyl-1,3-propanediol ((L+)-APPD) added thereto. The reactions were carried out under 35 psi hydrogen pressure at 55° C. After 24 hours, the reaction was terminated by filtration to remove the catalyst. The pH of the filtrate was adjusted to ca. 3 by adding 50% aqueous NaOH, and diluted with water (10 ml) and methanol(10 ml). The conversion was determined by HPLC under the following conditions;

Column HP LiChrospher 100 RP-18, 5 μm, 250×4 mm
Mobile Phase 2% Methanol in 0.1N $H_2PO_4$ (pH=3)
Flow rate 2 ml/min
Detector UV (215 nm)

The above procedure was repeated using other non-volatile acids such as p-toluene sulphonic acid, oxalic acid, maleic acid and phosphoric acid. The results are reported as items 1-6 and 9-12 on Table 1.

EXAMPLE 2

750 mg of 5% Pd/C and 10 g of L(+)-2-amino-1-phenyl-1,3-propanediol ((L+)-APPD) were added to 75 ml of TFA. The reaction was carried out under 35 psi hydrogen pressure at 55° C. After 21 hours, TFA was removed by evaporation and recovered by condensation. 50 ml of water was added and catalyst removed by filtration. The pH of the filtrate was adjusted to ca. 13 by adding 50% NaOH. After keeping the solution in refrigerator overnight, 7.9 g (yield=88%) of crystalline D-phenylalaninol was collected by filtration.

$[a]_D$= +23.0 (C=1.0, in 1N HCl)

EXAMPLE 3

In accordance with the procedure of Example 2, after pH adjustment to ca. 13, and evaporation of the water, 8.4 g (yield=93%) of D-phenylalaninol were obtained after vacuum distillation (0.3 mmHg, 120°–140° C.).

$[a]_D$= +22.2 (c=1.0, in 1N HCl)

EXAMPLE 4

Racemic APPD was hydrogenated and purified according to the procedure described in Example 2. 7.3 g (81%) of racemic phenylalaninol was obtained.

TABLE 1

Hydrogenation Reaction Using Various Acids

| Rxn No. | Acid | pKa | Acid amount (ml) | Mole Ratio*** | Solvent (ml) | Rxn. Time (hrs) | Conv. (%) |
|---|---|---|---|---|---|---|---|
| 1 | $H_2SO_4$ | −3 | 1 | 3 | $H_2O$, 15 | 21 | 10 |
| 2* | $H_2SO_4$ | −3 | 1 | 3 | $H_2O$, 15 | 24 | 14 |
| 3 | $H_2SO_4$ | −3 | 1 | 3 | EtOH, 15 | 28 | 49 |
| 4* | $H_2SO_4$ | −3 | 1 | 3 | EtOH, 15 | 24 | 28 |
| 5 | $H_2SO_4$ | −3 | 6 | 18 | $H_2O$, 10 | 24 | 82 |
| 6 | $H_2SO_4$ | −3 | 12 | 36 | $H_2O$, 4 | 24 | NA***** |
| 7 | 0.1M HCl in acetic acid | | 15 | | | 24 | 81 |
| 8 | 57% HI | | 15 | | | 24 | NA***** |
| 9 | p-TSA**** | −7 | 3.4 g | 3 | $H_2O$, 15 | 24 | 9 |
| 10 | oxalic acid | 1.2 | 1.6 g | 3 | EtOH, 15 | 24 | 0 |
| 11 | maleic acid | 1.8 | 1.7 g | 3 | EtOH, 15 | 24 | 0 |
| 12 | PA**** | | 15 | | | 24 | 45 |
| 13 | Acetic Acid | 4.7 | 15 | | | 24 | 4 |
| 14** | Acetic Acid | 4.7 | 15 | | | 2 | N.A.***** |
| 15** | TCA**** | 0.7 | 15 (23.8 g) | | | 2 | N.A.***** |
| 16 | TFA | 0.2 | 1.4 | 3 | EtOH, 15 | 24 | 2 |
| 17 | TFA | 0.2 | 15 | | | 24 | 99 |

*; Hydrogen gas was applied by bubbling at atmospheric pressure.
**; at 100° C.
***; Mole ratios of acids to APPD, [Acid]/[APPD]
****; p-TSA, p-Toluenesulfonic acid monohydrate. PA, Phosphoric acid (85%) TCA, trichloroacetic acid
*****; For Rxn 6, HPLC showed no desired product but 4 side-products (shorter RT). For Rxns 8 and 13, HPLC showed no desired product but a side-product. For Rxn 14, HPLC showed 85% of APPD, 8% of PAO, and 7% of side-product

EXAMPLE 5

2 g of APPD was dissolved in 15ml of TFA, and hydrogenated at 55° C. under 35 psi of hydrogen gas. The reaction conditions and results are described in Table 2.

TABLE 2

| catalyst | amount (mg) | [Cat]/[APPD] (%) | Rxn. Time (h) | Conv. (%) |
|---|---|---|---|---|
| 5% Pd/C | 150 | 0.3 | 2 | 51 |
| 3% Pt/C | 462 | 0.3 | 2 | 24 |

EXAMPLE 6

Direct N-blocked process of producing D-phenylalaninol 1.0 g of 10% Pd/C and 50 g of L(+)-2-amino-1-phenyl-1,3-propanediol were added into 150 ml of TFA. The reaction was carried out under 35 psi hydrogen pressure at 55° C. After 24 hours, TFA was removed by evaporation and recovered by condensation. 100 ml of water was added and catalyst removed by filtration. The pH of the filtrate was adjusted to ca. 13 by adding 50% aqueous NaOH. 55 ml of benzyl chloroformate was added dropwise at 4° C., while the final product (cbz-D-phenylalaninol)is precipitated. After filtration, white crystals were obtained by recrystallization from water/methanol (1:1). Yield; 77.5 g (90.8%); mp; 93.1°-93.9° C.; $[a]_D$= +48.0 (c=2.0, in methanol).

In accordance with the above procedure, but where in place of benzyl chloroformate as the N- blocking agent D-tert.-butyl dicarbonate is utilized there is obtained N-Boc-D-phenylalaninol.

We claim:

1. A process which comprises hydrogenating a phenylalaninol derivative of the structure,

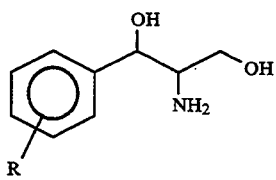

in which R=H, $C_1$–$C_7$ alkyl, or halogen in the presence of member selected from the group consisting of anhydrous hydrochloric acid and a strong volatile anhydrous organic acid in the presence of a hydrogenation catalyst to yield

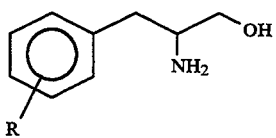

in which R=as above.

2. The process according to claim 1, wherein said acid is an organic acid.

3. The process according to claim 1, wherein the acid is hydrochloric acid.

4. The process of claim 1 wherein the phenylalaninol derivative is dissolved in a lower alkanoic acid of $C_1$ to $C_5$.

5. The process according to claim 2, wherein the organic acid is trichloroacetic acid or trifluoroacetic acid.

6. The process according to claim 1, wherein said catalyst is Pd or Pt.

7. The process according to claim 1, wherein the reaction temperature is between about 25° C. and about 100° C.

8. The process of claim 1 wherein the reaction is carried out at a hydrogen pressure of between about 1 and about 5 atmospheres.

9. The process according to claim 1, wherein the molar ratio of catalyst to APPD (2-amino-1-phenyl-1,3-propanediol) is 0.1 to 1.0%.

10. A process of preparing N-blocked phenylalaninol directly from a reaction mixture of the process of forming phenylalaninol without isolation of phenylalaninol which comprises carrying out the process of claim 1, removing the acid by evaporation and reacting the appropriate N- blocking agent with the residue in situ.

11. The process of claim 10 additionally comprising the step of recovering the product from the reaction mixture.

12. The process according to claim 2, wherein the organic acid is trichloroacetic acid.

* * * * *